United States Patent [19]

Reinink et al.

[11] 4,175,093

[45] Nov. 20, 1979

[54] PREPARATION OF α-CYANO ESTERS

[75] Inventors: Arend Reinink; Roger A. Sheldon, both of Amsterdam, Netherlands

[73] Assignee: Shell Oil Company, Houston, Tex.

[21] Appl. No.: 945,716

[22] Filed: Sep. 25, 1978

[30] Foreign Application Priority Data

Sep. 28, 1977 [GB] United Kingdom ............ 40335/77

[51] Int. Cl.² .................. C07C 120/00; C07C 121/66
[52] U.S. Cl. ............................................. 260/465 D
[58] Field of Search ................................. 260/465 D

[56] References Cited

U.S. PATENT DOCUMENTS

| | | | |
|---|---|---|---|
| 3,835,176 | 9/1974 | Matsuo et al. | 260/465 D |
| 3,996,244 | 12/1976 | Fujimoto et al. | 260/332.2 A |
| 4,024,163 | 5/1977 | Elliott et al. | 260/465 D |
| 4,072,752 | 2/1978 | Farooq et al. | 260/465 D |
| 4,091,110 | 5/1978 | Punja | 260/465 D |
| 4,113,763 | 9/1978 | Norton | 260/465 D |
| 4,123,451 | 10/1978 | Sheldon | 260/465 D |

FOREIGN PATENT DOCUMENTS 851900  8/1977  Belgium .

*Primary Examiner*—Dolph H. Torrence

[57] ABSTRACT

In the preparation of α-cyano esters from an acid halide and an aromatic aldehyde in the presence of water, a water-soluble cyanide, a substantially water-immiscible aprotic solvent and optionally a phase transfer catalyst, a stalled reaction is restarted by addition of an alkaline compound capable of generating cyanide ions.

30 Claims, No Drawings

PREPARATION OF α-CYANO ESTERS

BACKGROUND OF THE INVENTION

1. Field of the Invention

This invention relates to a process for the preparation of cyano-substituted carboxylic acid esters by reacting an acid halide, an aromatic aldehyde and a water-soluble cyanide.

2. Description of the Prior Art

A valuable group of esters consists of pesticides of the pyrethrin type, particularly those α-cyano esters as described in U.S. Pat. Nos. 3,835,176 and 3,996,244 and 4,024,163. These so-called synthetic pyrethroids have exceptionally good insecticidal and acaricidal properties while possessing a very low mammalian toxicity. This combination of properties makes these α-cyano esters of considerable interest to the agrochemical industry and much effort has been devoted to finding economic routes to these "synthetic pyrethroids".

U.S. Pat. Nos. 4,110,360–3 and 4,123,451 disclose the preparation of α-cyano esters from an acid halide, an aldehyde and a water-soluble cyanide. The present application is an improvement thereto.

SUMMARY OF THE INVENTION

The present invention relates to an improved process for the preparation of α-cyano esters in which process an acid halide and an aromatic aldehyde are reacted in the presence of water, a water-soluble cyanide optionally in the presence of a phase-transfer catalyst and a substantially aprotic solvent, the improvement comprising restarting a stalled reaction by addition of an alkaline compound capable of generating cyanide ions.

The process can be conducted as described in U.S. Pat. Nos. 4,110,260–3 and 4,123,451, the disclosures of which are incorporated herein by reference. However, during such a process, technical difficulties may arise resulting in insufficient amounts of water-soluble cyanide being present and the formation of acid anhydride. The hydrogen halide that is liberated simultaneously can form so much free hydrogen cyanide that the conversion of aromatic aldehyde comes to a standstill in the presence of unconverted aldehyde. In such case, the addition of an alkaline compound generating cyanide ions restores the reaction resulting in formation of the desired α-cyano ester product, usually until all the aromatic aldehyde has been fully converted.

Thus, the present invention is an improvement for the restart of a process for the preparation of an ester of formula I

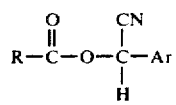

(I)

wherein R represents an optionally substituted hydrocarbyl group and A an optionally substituted aromatic group, which comprises the reaction of an aromatic aldehyde of the formula II

(II)

wherein Ar has the same meaning as in formula I, with an acid halide of formula III

(III)

wherein R has the same meaning as in formula I and X is a halogen atom having an atomic number of from 9–53, inclusive, and a water-soluble cyanide. Preferably, X is bromine and especially chlorine.

The alkaline compound capable of increasing the pH of the aqueous phase and thus of generating cyanide ions can be carbonates or hydroxides of alkali metals, for example, those of sodium or potassium, e.g. potassium hydroxide, sodium carbonate and the like.

The process according to the present invention is preferably carried out in the presence of a substantially water-immiscible aprotic solvent. A "substantially water-immiscible aprotic solvent" is defined as an aprotic solvent in which the solubility of water is not more than 5%v, at the reaction temperature adopted.

Examples of very suitable substantially water-immiscible aprotic solvents are alkanes or cycloalkanes, particular examples being n-hexane, n-heptane, n-octane, n-nonane, n-decane and their isomers (for example, 2-methylpentane, 3-methylpentane, 2-methylhexane, 3-methylhexane and 2,4,4-trimethylpentane) and cyclohexane and methylcyclohexane.

Other very suitable substantially water-immiscible aprotic solvents are aromatic hydrocarbons and chlorinated hydrocarbons, for example, benzene, toluene, o-, m- and p-xylene, the trimethylbenzenes, dichloromethane, 1,2-dichloroethane, chloroform, mono-chlorobenzene and 1,2-and 1,3-dichlorobenzene. Very good results have been obtained with toluene.

Other examples of substantially water-immiscible aprotic solvents are dialkyl ethers and substantially water-immiscible alkanones, for example, diisopropyl ether and diisobutyl ketone.

Mixtures of solvents, for example of alkanes, cycloalkanes and/or aromatic hydrocarbons may be employed, such mixtures of n-heptane and toluene or of n-heptane and one or more xylenes. Gasolines rich in alkanes are very suitable, for example, those with a boiling range at atmospheric pressure between 40° C. and 65° C. or 80° C. and 110° C. and particularly between 60° C. and 80° C. Mixtures of xylenes are also very suitable.

The esters of formula I may be prepared in the presence or absence of a phase-transfer catalyst. The phase-transfer catalyst may be any reagent which is capable of accelerating interphase reactions in aqueous/organic two-phase systems.

The phase-transfer catalyst may be an onium compound, particularly (1) a quaternary onium compound of formula IV

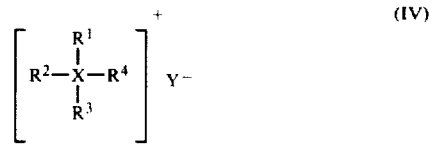

(IV)

wherein X represents a nitrogen, phosphorous or arsenic atom and each of the groups $R^1$, $R^2$, $R^3$ and $R^4$ represents a monovalent ion.

Preferably, $R^1$, $R^2$, $R^3$ and $R^4$ each independently is an alkyl group of 1 to 18 carbon atoms, an aralkyl or alkaryl group of 7 to 10 carbon atoms or an aryl group of 6 to 12 carbon atoms; or (2) a sulfonium compound of the formula V

wherein $R^5$, $R^6$ and $R^7$ each individually represents an alkyl group and Y a monovalent ion. Preferably, $R^5$, $R^6$ and $R^7$ each independently is an alkyl group of 1 to 18 carbon atoms.

In formulas IV and V above, Y can be hydroxide, halide, (alkyl)sulfate, (alkyl)sulfonate, tetrafluoroborate, phosphate, nitrate or alkyl- or aryl-carboxylate. For example, Y can be chloride, bromide, iodide, methylsulfate, ethylsulfate, tosylate, acetate, formate, citrate, tartrate, benzoate or the like.

Examples of suitable onium compounds are tetra-n-butylammonium bromide, tetra-n-butylammonium chloride, methyltri-2-methylphenylammonium chloride, tetramethylphosphonium iodide, tetra-n-butylphosphonium bromide, methyltriphenylarsonium iodide, ethyl-2-methylpentadecyl-2-methylundecylsulfonium ethylsulfate, methyldinonylsulfonium methylsulfate and n-hexadecyldinonylsulfonium methylsulfate, methyltrioctylammonium chloride and n-hexadecyldimethylsulfonium iodide. Further suitable onium compounds are described in U.S. Pat. Nos. 3,917,667, 4,008,287 and 4,012,430. Very good results have been obtained with quaternary ammonium compounds.

The onium compound may be a hydroxide or salt and is used as the functional portion of a strongly basic anion exchange resin having a structural portion (polymer matrix) and a functional portion (ion-active group). Of special importance are polystyrene resins, such as copolymers of aromatic monovinyl compounds and aromatic polyvinyl compounds, particularly styrene/divinylbenzene copolymers. The functional portion is a quaternary ammonium, phosphonium or arsonium group. Examples of strongly basic anion exchange resins which may be employed are those derived from trimethylamine (such as the products known under the trade names of "Amberlite IRA-400," "Amberlite IRA-401," "Amberlite IRA-402," "Amberlite IRA-900," "Duolite A-101-D," "Duolite ES-111," "Dowex 1," "Dowex 11," "Dowex 21K" and "Ionac A-450" (all ten trade names are trademarks) and those derived from dimethylethanolamine (such as the products known under the trade names of "Amberlite IRA-410," "Amberlite IRA-911," "Dowex 2," "Duolite A-102-D", "Ionac A-542" and "Ionax A-550" (all six trade names are trademarks). Very good results have been obtained with those derived from trimethylamine. When these catalysts are available in a neutralized form, for instance in the chloride form, they must be activated to the hydroxyl form by treatment with an aqueous alkali metal hydroxide, for example sodium hydroxide, and washed with water to remove salt anions before use.

More particularly, one preferred subclass of catalysts of formula II are those in which $R^1$, $R^2$, $R^3$ and $R^4$ each independently is an alkyl group of 1 to about 8 carbon atoms such as methyl-trioctylammonium chloride, tributylammonium bromide, tetra-n-butylammonium hydroxide, bromide or chloride, methyl-tri-2-methylheptylammonium chloride, tetramethylammonium bromide, tetrabutylphosphonium bromide or tetraethylammonium bromide. Other suitable catalysts of this type are known under the trade names "Hyamine 1663," "Hyamine 2389," "Hyamine 3500," "Aliquat 336" and "Adogen 464" (all five trade names are trademarks).

Another preferred subclass of catalysts of formula II are those containing one or more phenyl or benzyl groups as $R^1$, $R^2$, $R^3$ and $R^4$ such as benzyltriethylammonium chloride or ethyltriphenylphosphonium bromide or the like.

Examples of catalysts of formula III are triethylsulfonium iodide di-sec-decyldimethylsulfonium methyl sulfate, sec-dodecyl-sec-hexadecylethylsulfonium ethyl sulfate, sec-hexadecyldimethylsulfonium iodide, sec-hexadecylmethylethylsulfonium tosylate, sec-hexadecyldimethylsulfonium tosylate, trimethylsulfonium bromide and di-n-butylmethylsulfonium iodide. Preferred catalysts of formula III are those in which $R^5$, $R^6$ and $R^7$ each independently is an alkyl group of 3 to 16 carbon atoms. The preparation of catalysts of formula III is described in U.S. Pat. No. 3,917,667.

Other suitable phase transfer catalysts are macrocyclic polyethers known as "crown ethers." These compounds, together with their preparation, are described in the literature, for example in Tetrahedron Letters No. 18(1972) pp. 1793-1796, and are commonly designated by reference to the total number of atoms forming the macrocyclic ring together with the number of oxygen atoms in that ring. Thus the macrocyclic polyether whose formal chemical name is 1,4,7,10,13,16-hexaoxacyclooctadecane is designated as "18-crown-6." Other examples of suitable macrocyclic polyethers are 3,4-benzo-1,6,9,12,15,18,21-heptaoxacyclotricos-3-ene and 3,4-benzo-1,6,9,12,-tetraoxacyclotetradec-3-ene. 18-Crown-6 is particularly suitable. Further suitable macrocyclic polyethers and their preparation are described in U.S. Pat. No. 3,562,295, British Pat. No. 1,108,921 and Netherlands publication No. 7,602,604.

Thus, useful macrocyclic polyethers can have from 15 to 30 ring atoms in the polyether ring and consist of from 5 to 10 —O—X— units wherein X for a particular compound is either

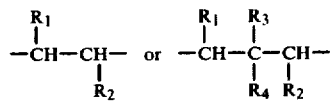

in which $R_1$, $R_2$, $R_3$ and $R_4$ are radicals independently selected from the group consisting of hydrogen and alkyl radicals having from 1 to 4 carbon atoms with the proviso that when the —O—X— units comprise

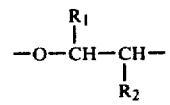

one of X can be (b). For example:
1,4,7,10,13,16-hexaoxacyclooctadecane,
1,4,7,10,13-pentaoxacyclopentadecane,
1,4,7,10,13,16,19-heptaoxacycloheneicosane,
1,4,7,10,13,16,19,22-octacyclotetracosane, and
1,4,7,10,13,16,19,22,25,27-decaoxacyclotricontane Other useful macrocyclic polyethers can contain 4 to 80 atoms, preferably 14–28 are ring atoms of which at least 4 and preferably 5 to 8 are oxygen atoms. Up to 10 carbon atoms can be present between one or more pairs of oxygen atoms with at least 1 aromatic nucleus attached to the polyether ring by means of vicinal carbon atoms of the aromatic nucleus. The aromatic nucleus may be optionally substituted by halogen, alkyl, cyano, amino, nitro, hydroxy and carboxy radicals. For example:

2,3-benzo-1,4,7,10-tetraoxacyclododeca-2-ene,
2,3,8,9-dibenzo-1,4,7,10-tetraoxacyclododeca-2,8-diene,
2,3,9,10-dibenzo-1,4,8,11-tetraoxacyclotetradeca-2,9-diene,
2,3,9,10-bis(t-butylbenzo)-1,4,8,11-tetraoxacyclotetradeca-2,9-diene,
2,3,8,9-dibenzo-1,4,7,10,13-pentaoxacyclopentadeca-2,8-diene,
2,3,9,10-dibenzo-1,4,8,11,14-pentaoxacyclohexadeca-2,9-diene,
2,3,11,12-dibenzo-1,4,7,10,13-pentaoxacyclooctadeca-2,11-diene,
2,3,8,9-dibenzo-1,4,7,10,13,16-hexaoxacyclooctadeca-2,8,diene,
2,3,11,12-dibenzo-1,4,7,10,13,16-hexaoxacyclooctadeca-2,11-diene,
2,3,11,12-bis(t-butylbenzo)-1,4,7,10,13,16-hexaoxacyclooctadeca-2,11-diene,
2,3,11,12-bis(2',3'-naphtho)-1,4,7,10,13,16-hexaoxacycloocta-2,11-diene,
2,3,12,13-dibenzo-1,4,11,14-tetraoxacycloeicosa-2,12-diene,
2,3,11,12-dibenzo-1,4,7,10,13,19-hexacyclodocosa-2,11-diene,
2,3,14,15-dibenzo-1,4,10,13,16,19,22-octaoxacyclotetracosa-2,14-diene,
2,3-benzo-1,4,7,10,13,16-hexaoxacyclooctadeca-2-ene,
2,3,8,9,14,15-tribenzo-1,4,7,10,13,16-hexaoxacyclooctadeca-2,8,14-triene,
2,3,9,10-dibenzo-1,4,8,11,14,17-hexaoxacyclononadeca-2,9-diene,
2,3,8,9,14,15-tribenzo-1,4,7,10,13,16-hexaoxacyclononadeca-2,8,14-triene,
2,3,11,12-dibenzo-1,4,7,10,13,16,19-heptaoxacyclohenicosa-2,8,14-triene,
2,3,8,9,14,15-tribenzo-1,4,7,10,13,16,19,22-octaoxacyclotetracosa-2,8,14-triene,
2,3,8,9,14,15,20,21-tetrabenzo-1,4,7,10,13,16,19,22-octaoxacyclotetracosa-2,8,14-triene,
2,3,15,16-dibenzo-1,4,9,14,17,22-hexaoxacyclohexacosa-2,15-diene,
2,3-(t-butylbenzo)-1,4,7,10,13,16-hexaoxacyclooctadeca-2-ene,
2,3-benzo-1,4,7,10,13-pentaoxacyclopentadeca-2-ene,
2,3-(t-butylbenzo)-1,4,7,10,13-pentaoxacyclopentadeca-2-ene, and
2,3,16,17-dibenzo-1,4,15,18-tetraoxacyclooctacosa-2,16-diene.

Other suitable macrocyclic polyethers have the formulas VI, VII and VIII

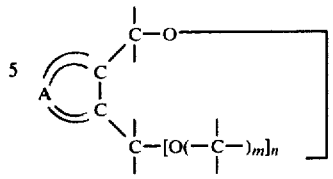

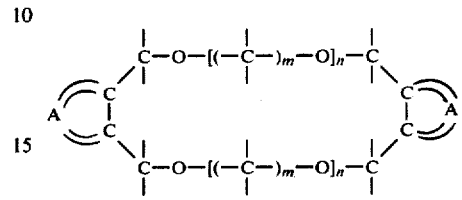

and

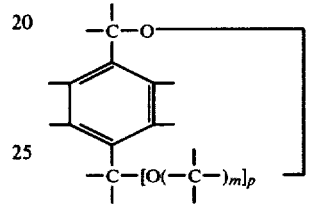

in which formula A and the two carbon atoms attached to A together represent a carbocyclic aromatic or hetero-aromatic group, m, n and p are integers from 2 to 10 inclusive, of at least 2 and of at least 3 respectively.

Examples of macrocyclic polyethers of formulas VI, VII, and VIII include:

3,4-benzo-1,6,9,12,15,18,21-heptaoxacyclotricos-3-ene,
3,4-benzo-1,6,9,12-tetraoxacyclotetradec-3-ene,
3,4,17,18-dibenzo-1,6,9,12,15,20,23,26-octaoxacyclooctacos-3,17-diene,
3,4-benzo-1,6,9-trioxacycloundec-3-ene,
3,4-benzo-1,6,9,12,15-pentaoxacycloheptadec-3-ene,
3,4-1,6,9,12,15,18-hexaoxacycloeicos-3-ene,
3,4-benzo-1,6,9,12,15,18,21,24-octaoxacyclohexacos-3-ene,
3,4,14,15-dibenzo-1,6,9,12,17,20-hexaoxacyclodocos-3-ene,
3,4,17,18-dibenzo-1,6,9,12,15,20,23,26-octaoxacyclooctacos-3,17-diene,
3,4,20,21-dibenzo-1,6,9,12,15,18,23,26,29,32-decaoxacyclotetratriacont-3,20-diene,
[3,4-c]furo-1,6,9,12,15,18,21,24-octaoxacyclohexacos-3-ene,
[3,4-c]furo-1,6,9,12-tetraoxacyclotetradecane,
[3,4-c]furo-1,6,9,12,15-pentaoxacycloheptadecane,
[3,4-c]furo-1,6,9,12,15,18-hexaoxacycloeicosane,
[3,4-c]furo-1,6,9,12,15,18,21-heptaoxacyclotricosane,
[3,4-c]furo-1,6,9,12,15,18,21,24-octaoxacyclohexacosane,
3,4,14,15-difuro-1,6,9,12,17,20-hexaoxacyclodocosane,
3,4,17,18-difuro-1,6,9,12,15,18,23,26-octaoxacyclooctacosane,
3,4,20,21-difuro-1,6,9,12,15,18,23,26,29,32-decaoxacyclotetratriacontane,
[3,4-c]furo-1,6,9,12-tetraoxacyclotetradec-3-ene,
[3,4-c] [17,18-c]difuro-1,6,9,12,15,20,23,26-octaoxacyclooctacos-3,17-diene,

[3,4-c]-2¹,5¹-dimethylthieno-1,6,9,12,15,18-hexaoxacycloeicos-3-ene,
3,4-(4¹,5¹-methylene-dioxybenzo)-1,6,9,12,15,18–21-heptaoxacyclotricos-3-ene,
3,6-benzo-1,8,11,14-tetraoxacyclohexadec-3,5-diene,
3,6-benzo-1,8,11,14,17,pentaoxacyclononadec-3,5-diene,
3,6-benzo-1,8,11,14,17,20-hexaoxacyclodocosa-3,5-diene,
3,6-benzo-1,8,11,14,17,20,23-heptaoxacyclopentacosa-3,5-diene,
3,6-benzo-1,8,11,14,17,20,23,26-octaoxacyclooctacosa-3,5-diene, and
3,6-benzo-1,8,11,14,17,20,23,26,29-nonaoxacyclohentriaconta-3,5-diene.

Other phase-transfer catalysts are surface-active agents. A "surface-active agent" is defined as in Kirk-Othmer, "Encyclopedia of Chemical Technology," second edition, volume 19(1969), page 508: "An organic compound that encompasses in the same molecule two dissimilar structural groups, one being water-soluble and one being water-insoluble."

The surface-active agent is preferably non-ionic. Non-ionic synthetic surface-active agents may be broadly defined as compounds aliphatic or alkylaromatic in nature which do not ionize in water solution. For example, a well known class of non-ionic agents is made available on the market under the trade name of "Pluronic." These compounds are formed by condensing ethylene oxide with a hydrophobic base formed by condensing ethylene oxide with a hydrophobic base formed by the condensation of propylene oxide with propylene glycol. The hydrophobic portion of the molecule, which of course exhibits water insolubility, has a molecular weight of from about 1,500 to 1,800. The addition of polyoxyethylene radicals to this hydrophobic portion tends to increase the water solubility of the molecule as a whole and the liquid character of the product is retained up to the point where the polyoxyethylene content is about 50% of the total weight of the condensation product.

Other suitable nonionic agents include:

(1) The polyethylene oxide condensates of alkyl phenols, e.g., the condensation products of alkyl phenyls having an alkyl group containing from about 6 to 12 carbon atoms in either a straight chain or branched chain configuration, with ethylene oxide, the said ethylene oxide being present in amounts equal to 10 to 25 moles of ethylene oxide per mole of alkyl phenol. The alkyl substituent in such compounds may be derived from polymerized propylene, diisobutylene, octene, or nonene, for example;

(2) Those derived from the condensation of ethylene oxide with the product resulting form the reaction of propylene oxide and ethylenediamine. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylenediamine and excess propylene oxide, said hydrophobic base having a molecular weight of the order of 2,500 to 3,000 are satisfactory;

(3) The condensation product of aliphatic alcohols having from 8 to 18 carbon atoms, in either straight chain or branched chain configuration, with ethylene oxide, e.g., a coconut alcohol-ethylene oxide condensate having from 10 to 30 moles of ethylene oxide per mole of coconut alcohol, the coconut alcohol fraction having from 10 to 14 carbon atoms;

(4) Long chain tertiary amine oxides corresponding to the following general formula, $R_1R_2R_3N \rightarrow O$, wherein $R_1$ is an alkyl radical of from about 8 to 18 carbon atoms, and $R_2$ and $R_3$ are each methyl or ethyl radicals. The arrow in the formula is a conventional representation of a semi-polar bond. Examples of amine oxides suitable for use in this invention include dimethyldodecylamine oxide, dimethyloctylamine oxide, dimethyldecylamine oxide, dimethyltetradecylamine oxide, dimethylhexadecylamine oxide;

(5) Long chain tertiary phosphine oxides corresponding to the following formula $RR'R''P \rightarrow O$, wherein R is an alkyl, alkenyl or monohydroxyalkyl radical ranging from 10 to 18 carbon atoms chain length and R' and R'' are each alkyl or monohydroxyalkyl groups containing from 1 to 3 carbon atoms. The arrow in the formula is a conventional representation of a semi-polar bond. Examples of suitable phosphine oxides are:
dimethyldodecylphosphine oxide,
dimethyltetradecylphosphine oxide,
ethylmethyltetradecylphosphine oxide,
cetyldimethylphosphine oxide,
dimethylstearylphosphine oxide,
cetylethylpropylphosphine oxide
diethyldodecylphosphine oxide,
diethyltetradecylphosphine oxide,
bis(hydroxymethyl)dodecylphosphine oxide,
bis(2-hydroxyethyl)dodecylphosphine oxide,
2-hydroxypropylmethyltetradecylphosphine oxide,
dimethyloleylphosphine oxide, and
dimethyl-2-hydroxydodecylphosphine oxide.

(6) Dialkyl sulfoxides corresponding to the following formula, $RR'S \, O$, wherein R is an alkyl, alkenyl, beta- or gamma-monohydroxyalkyl radical or an alkyl or beta- or gamma-monohydroxyalkyl radical containing one or two other oxygen atoms in the chain, the R groups ranging from 10 to 18 carbon atoms in chain length, and wherein R' is methyl or ethyl.
Examples of suitable sulfoxide compounds are:
dodecylmethyl sulfoxide,
tetradecylmethyl sulfoxide,
3-hydroxytridecylmethyl sulfoxide,
2-hydroxydodecylmethyl sulfoxide,
3-hydroxy-4-decoxybutylmethyl sulfoxide,
3-hydroxy-4-dodecoxybutylmethyl sulfoxide,
2-hydroxy-3-decoxypropylmethyl sulfoxide,
2-hydroxy-3-dodecoxypropylmethyl sulfoxide,
dodecylethyl sulfoxide, and
2-hydroxydodecylethyl sulfoxide.

(7) The ammonia, monoethanol an diethanol amides of fatty acids having an acyl moiety of from about 8 to about 18 carbon atoms;

(8) A sorbitan monoester with a long chain fatty acid of 8 to 20 carbon atoms; or (9) An alkylbenzene containing a straight-chain alkyl group. Suitable alkylbenzenes contain an alkyl group of 8 to 20 carbon atoms.

Preferred surface-active agent are poly(alkyleneoxy) derivatives formed by reacting a higher alcohol, alkylphenol or fatty acid with ethylene oxide or propylene oxide. Suitable alcohols, alkylphenols or fatty acids contain an alkyl group of from 8 to 20 carbon atoms and the number of alkyleneoxy units is in the range of 1 to 50. It is perferable to use an alcohol ethoxylate such as the ethoxylates derived by ethoxylation of primary or secondary, straight-chain or branched alcohols. A single alcohol may be used e.g., octyl alcohol, decyl alcohol, dodecyl alcohol, but preferably a mixture of alcohols is used. The mixture of alcohols may contain small amounts of alcohols below $C_7$ and above $C_{13}$ but at least 90%w, and preferably at least 95%w, of the alcohols thereof are in the $C_9$ to $C_{13}$ range. Preferred mixtures of alcohols are those mixtures of $C_9$ to $C_{11}$ alcohols such as those prepared by hydroformylation of olefins. The amount of ethylene oxide used to prepare such ethoxylates is suitably such as to provide an average from 1 to 13 moles, and preferably 5 to 9 moles, of ethylene oxide per mole of alcohol (or alcohol mixture). Examples of such ethoxylates are "Dobanol$_{45-11}$" formed from a $C_{14}$ to $C_{15}$ straight-chain alcohol mixture and containing an average of eleven ethyleneoxy units or preferably "Dobanol$_{91-6}$" formed from a $C_9$ to $C_{11}$ straight-chain alcohol mixture with an average of six ethyleneoxy units (both trade names are registered trademarks).

The molar ratio of the phase-transfer catalyst to the aromatic aldehyde of formula II may vary within wide limits, but is suitably from about 1:5 to about 1:10,000. Low molar ratios will require long reaction times, while high molar ratios will increase the cost involved in producing a given quantity of ester. Thus, the choices of reaction time and molar ratio of catalyst to benzaldehyde are interdependent and will, in any individual instance, be dictated by local economic factors. Very good results are usually obtained at molar ratios of from about 1:10 to 1:500 or even from about 1:10 to about 1:100.

The molar ratio of water-soluble cyanide to aromatic aldehyde is suitable from 1.5:1 to 1.0:1.0 and preferably from 1.3:1 to 1.02:1.00. By "water-soluble cyanide" is meant a water-soluble salt of hydrogen cyanide. Of the water-soluble cyanides, alkali metal cyanides and alkaline-earth-metal cyanides are preferred. Sodium cyanide is particularly preferred because it affords the ester of formula I in the shortest reaction time.

The optionally substituted aromatic group Ar in the aromatic aldehyde of the formula II may be carbocyclic or heterocyclic. Examples of carbocyclic groups are phenyl, 1-naphthyl, 2-naphthyl and 2-anthryl groups. Heterocyclic aromatic groups are derived from heteroaromatic compounds which are defined as in Kirk-Othmer, "Encyclopedia of Chemical Technology", Second Edition, Volume 2 (1963), page 702; obtained by replacement of one or more carbon atoms of a carbocyclic aromatic compound by a hetero-atom—for example, pyridine, pyrimidine, pyrazine, quinoline and isoquinoline—and also include those heterocyclic compounds having five-membered rings which show aromatic characteristics and are mentioned on page 703 of said volume, for example, thiophene, pyrrole, furan, indole and benzothiophene. As an aromatic group, an optionally substituted phenyl group is very suitable. Examples of substituents are hydrocarbyl and hydrocarbyloxy groups and the like.

The symbol Ar in formula II preferably represents a group of formula IX

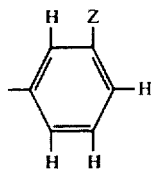

in which Z represents a phenoxy, a phenylthio or a benzyl group. More particularly, Z represents a phenoxy group, because this substituent generally gives rise to the most active form of the pyrethroid insecticides.

The group R in formula III is defined as an optionally substituted hydrocarbyl group. The process is particularly useful when the acid halide is the halide of a pyrethroid acid. The group R may be, for example, an alkyl group, a cycloalkyl group or an aryl group. Very good results have been obtained with alkyl and cycloalkyl groups. The alkyl group may be linear or branched and preferably contains up to 10 carbon atoms. The alkyl groups may have a primary, secondary, tertiary or a quaternary carbon atom bound to a group —C(O)—. Examples of alkanoic halides are acetic, isobutyric, 2,2-dimethylpropanic, and 2-methylbutanoic halides. The alkyl group may carry substituents, such as hydrocarbyloxy or substituted phenyl groups, e.g. a halophenyl group or the like.

For example, R is a substituted alkyl group of the formula X

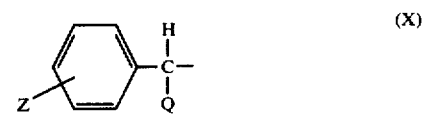

wherein Z represents a halogen atom having an atomic number of from 9 to 35, inclusive, e.g., chlorine, or an alkyl or alkoxy group containing from 1 to 4 carbon atoms, e.g., methyl, tert-butyl, methoxy or the like, and Q represents an alkyl group of from 1 to 6 carbon atoms, especially a branched chain group such as an isopropyl group. Very good results have been obtained with 2-(4-chlorophenyl)-3-methylbutanoic chloride.

The cycloalkyl group itself, represented by R, preferably contains 3 to 6 carbon atoms and has an optional substituents one or more groups selected from alkyl, alkenyl or haloalkenyl, each of which suitably contains up to 8 carbon atoms. Examples of cycloalkyl groups are cyclopropyl, cyclobutyl and cyclohexyl groups.

For example, R is a substituted cyclopropyl group of formula XI

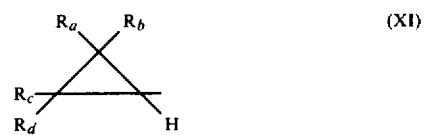

wherein $R_a$ and $R_b$ each independently represents an alkyl group containing from 1 to 6 carbon atoms, especially methyl, or a halogen atom having an atomic number of from 9 to 35, inclusive, especially a chlorine atom, or when $R_a$ represents a hydrogen atom then $R_b$ represents an alkenyl group containing from 2 to 6 carbon atoms optionally substituted by from 1 to 3 halogen atoms, especially a chlorine or bromine atom, e.g., $R_b$ is isobutenyl, 2,2-dichlorovinyl or dibromovinyl; $R_c$ and $R_d$ each independently represents an alkyl group containing from 1 to 6 carbon atoms; or at least one of $R_a$ and $R_b$ together or $R_c$ and $R_d$ together represents an alkylene group containing from 2 to 6 carbon atoms, especially 3 carbon atoms.

Very good results have been obtained with optionally substituted cyclopropanecarboxylic halides, particularly with 2-(2,2-dichlorovinyl)-3,3-dimethylcyclopropanecarboxylic halides. Another example of an acid halide of formula III is 2,2,3,3-tetramethylcyclopropanecarboxylic halide. The halides of formula III may have cis or trans structure or may be a mixture of such structures and may be a pure optical isomer or a mixture of optical isomers. Halides having a cis structure are particularly interesting as pesticide intermediates.

The process is of particular interest to prepare pesticidally active esters, for example: when the aromatic aldehyde of formula II is 3-phenoxybenzaldehyde and the acid halide of formula III is an aralkyl acid halide such as 2-(4-chlorophenyl)-3-methylbutanoic halide, or a substituted-cyclopropanecarboxylic halide, 2-(2,2-dibromovinyl)-3,3-dimethylcyclopropanecarboxylic halide or 2-(2,2-dichlorovinyl)-3,3-dimethylcyclopropanecarboxylic halide, because the esters then formed are α-cyano3-phenoxybenzyl 2-(4-chlorophenyl)-3-methylbutanoate, α-cyano-3-phenoxybenzyl 2,2,3,3-tetramethylcyclopropanecarboxylate, α-cyano-3-phenoxybenzyl 2-(2,2-dibromovinyl)-3,3-dimethylcyclopropanecarboxylate and α-cyano-3-phenoxybenzyl 2-(2,2-dichlorovinyl)-3,3-dimethylcyclopropanecarboxylate, respectively, all of which are pesticidally active compounds disclosed in U.S. Pat. Nos. 3,835,176, 3,996,244 and 4,024,163.

The process according to the present invention may be conducted starting from unsaturated or saturated aqueous solutions of water-soluble cyanide, in the latter case in the presence of absence of solid water-soluble cyanide. The use of solid water-soluble cyanide has a cost saving effect, since smaller volumes of water can be handled.

The temperature at which the process is conducted is suitably above 0° C., for example, from about 0° C. to about 80° C., and is preferably in the range of from about 15° C. to about 40° C. The process has the advantage that it is suitably carried out at ambient temperatures.

Another advantage of the process according to the present invention is that the molar ratio of the acid halide of formula III to the aromatic aldehyde of formula II may be about 1:1 or slightly in excess thereof. The said molar ratio is preferably in the range of from about 1.1:1.0 to about 1.0:1.0.

The process according to the present invention may be carried out by gradual addition of the water-soluble cyanide to a mixture, preferably a stirred mixture, of the other starting compounds. Alternatively, all materials may be combined and the reaction allowed to take place with vigorous stirring of the reaction mixture.

The ester of formula I may be recovered from the reaction mixture obtained by isolating the organic phase from the aqueous phase, extracting the aqueous phase with a hydrocarbon solvent, combining the extract phase with the organic phase, washing the mixture thus obtained with water, drying the washed mixture and evaporating the solvent from the dried mixture.

Illustrative Embodiments

The present invention is further illustrated by the following Embodiments. In these embodiments, the reaction mixtures were analysed by gas-liquid chromatography to determine the various yields. The solutions were dried over anhydrous sodium sulphate. Solvents were flashed off in a film evaporator at the pressure of 15 mm Hg. All ester yields were calculated on starting aldehyde.

EMBODIMENT I

The experiment described below was carried out in a cylindrical, round-bottomed, glass-lined reactor provided with an inlet at the top, an outlet at the bottom, an impeller stirrer having a diameter of 0.91 m, a thermowell and a dip pipe for taking samples. The thermowell and the dip pipe also served as baffles. The reactor had a height (measured along the vertical wall) of 1.98 m, an inner diameter of 1.83 m and a capacity of 4.5 m$^3$. A cooling or heating liquid could be passed through a jacket surrounding the vertical wall of the reactor. The stirrer speed was 90 revolutions per minute. The reactants were 2-(2,2-dichlorovinyl)-3,3-dimethylcyclopropanecarboxylic acid chloride, 3-phenoxybenzaldehyde and sodium cyanide in the presence of water, xylene and tetrabutylammonium bromide catalyst. After formation of a substantial amount of the desired α-cyano-3-phenoxybenzyl 2-(2,2-dichlorovinyl)-3,3-dimethylcyclopropanecarboxylate product ester, the reaction came to a standstill and the reactor contained:

| | |
|---|---|
| 2-(2,2-dichlorovinyl)-3,3-dimethylcyclopropane-carboxylic anhydride | 127 mol |
| 3-phenoxybenzaldehyde | 99 mol |
| sodium cyanide | 140 mol |
| tetrabutylammonium bromide | 5 mol |
| alpha-cyano-3-phenoxybenzyl 2-(2,2-dichlorovinyl)-3,3-di-methylcyclopropanecarboxylate | 1156 mol |
| xylene | 550 kg |
| water | 305 kg |
| sodium chloride | 1410 mol |
| hydrogen cyanide | 254 mol |

After nine hours stirring at 20° C., the mixture in the reactor had still this composition. An aqueous solution of sodium carbonate (240 mol of Na$_2$CO$_3$ in 225 kg of water) was added to the reactor and stirring was continued for 30 minutes at 20° C. Then, stirring was stopped and the reaction mixture allowed to settle for one hour, resulting in a sharp separation of the aqueous phase from the organic phase. The 3-phenoxybenzaldehyde had been fully converted into alpha-cyano-3-phenoxybenzyl 2-(2,2-dichlorovinyl)-3,3-dimethylcyclopropanecarboxylate.

We claim:

1. In a process for the preparation of an ester of formula I

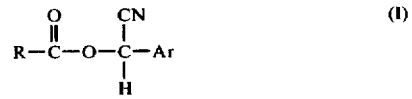
(I)

wherein Ar represents a phenyl group substituted at the 3-position by a phenoxy, a phenylthio or a benzyl group, and

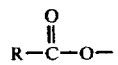

represents the residue of a pyrethroid acid, in which process an aromatic aldehyde of formula II

wherein Ar has the same meaning as in formula I, is treated with an acid halide of formula III

wherein R has the same meaning as in formula I, and X is a halogen atom having an atomic number of from 9 to 53, inclusive, in the presence of water and a water-soluble cyanide and optionally in the presence of a phase-transfer catalyst the improvement comprising restarting a stalled reaction by addition of an alkaline compound selected from alkali metal carbonates and hydroxides in an amount sufficient to increase the pH of the aqueous phase and generate cyanide ions.

2. A process according to claim 1, conducted in the presence of a substantially water-immiscible aprotic solvent.

3. A process according to claim 2 wherein the substantially water-immiscible aprotic solvent is selected from alkanes, cycloalkanes, aromatic hydrocarbons, chlorinated hydrocarbons, dialkyl ethers, alkanones, or mixtures thereof.

4. A process according to claim 3 wherein the substantially water-immiscible aprotic solvent is an alkane or cycloalkane or a mixture thereof.

5. A process according to claim 4 wherein the alkane is n-heptane.

6. A process according to claim 4 wherein the cycloalkane is cyclohexane.

7. A process according to claim 3 wherein the substantially water-immiscible aprotic solvent is an aromatic solvent or a mixture of aromatic hydrocarbons.

8. A process according to claim 7 wherein the aromatic solvent is toluene.

9. A process according to claim 3 wherein the substantially water-immiscible aprotic solvent is a chlorinated hydrocarbon.

10. A process according to claim 3 wherein the substantially water-immiscible aprotic solvent is a dialkyl ether.

11. A process according to claim 3 wherein the substantially water-immiscible aprotic solvent is a substantially water-immiscible alkanone.

12. A process according to claim 3 which is conducted in the presence of a phase transfer catalyst.

13. A process according to claim 12 wherein the phase transfer catalyst is a quaternary onium compound of the formula

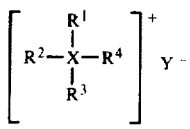

wherein X represents a nitrogen, phosphorous or arsenic atom; $R^1$, $R^2$, and $R^3$ and $R^4$ each individually represents an alkyl, aralkyl, alkaryl or aryl group; and Y represents a monovalent ion, or a sulfonium compound of the formula

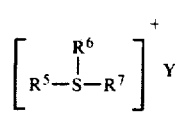

wherein $R^5$, $R^6$ and $R^7$ each individually represents an alkyl group; and Y is a monovalent ion.

14. A process according to claim 12 wherein the phase transfer catalyst is a macrocyclic polyether.

15. A process according to claim 12 wherein the phase transfer catalyst is a non-ionic surface-active agent.

16. A process according to claim 12 wherein the molar ratio of the amount of phase transfer catalyst to aromatic aldehyde of formula I is from 1:15 to 1:10,000.

17. A process according to claim 3 wherein the molar ratio of the amount of acid halide of formula III to the amount of aromatic aldehyde of formula II is in the ratio of 1:1 or slightly in excess thereof.

18. A process according to claim 3 conducted at a temperature from about 0° C. to about 80° C.

19. A process according to claim 3 conducted in the presence of solid water-soluble cyanide.

20. A process according to claim 3 wherein the water-soluble cyanide is an alkali metal or an alkaline earth metal cyanide.

21. A process according to claim 20, wherein the water-soluble cyanide is sodium cyanide.

22. A process according to claim 1 wherein the aromatic group Ar is phenoxyphenyl.

23. A process according to claim 1 wherein the acid halide is the halide of a pyrethroid acid of formula III wherein R is (a) a substituted alkyl group of the formula

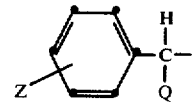

wherein Z represents a halogen atom having an atomic number of from 9 to 35, inclusive, or an alkyl or alkoxy group containing from 1 to 4 carbon atoms and Q represents an alkyl group containing from 1 to 6 carbon atoms or (b) is a substituted cyclopropyl group of the formula

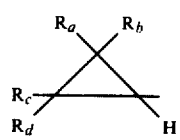

wherein $R_a$ and $R_b$ each independently represent an alkyl group containing from 1 to 6 carbon atoms or a halogen atom having an atomic number of from 9 to 35, inclusive, or when $R_a$ represents a hydrogen atom then $R_b$ represents an alkenyl group containing from 2 to 6 carbon atoms optionally substituted by from 1 to 3 halogen atoms, $R_c$ and $R_d$ each independently represents an alkyl group containing from 1 to 6 carbon atoms or at least one of $R_a$ and $R_b$ together or $R_c$ and $R_d$ together represents an alkylene group containing from 2 to 6 carbon atoms.

24. A process according to claim 23 wherein the acid halide is 2-(4-chlorophenyl)-3-methylbutanoic halide.

25. A process according to claim 23 wherein the acid halide is 2,2-dimethylpropanoic halide.

26. A process according to claim 23 wherein the acid halide is an optionally substituted cyclopropanecarboxylic halide.

27. A process according to claim 26 wherein the acid halide is 2,2,3,3-tetramethylcyclopropanecarboxylic halide.

28. A process according to claim 26 wherein the acid halide is 2-(2,2-dichlorovinyl)-3,3-dimethylcyclopropanecarboxylic halide.

29. A process according to claim 26 wherein the acid halide is 2-(2,2-dibromovinyl)-3,3-dimethylcyclopropanecarboxylic halide.

30. A process according to claim 1 wherein the alkaline compound is sodium carbonate.

* * * * *